(12) United States Patent
Gillespie, III et al.

(10) Patent No.: US 8,048,029 B2
(45) Date of Patent: Nov. 1, 2011

(54) INJECTOR APPARATUS

(75) Inventors: Richard David Gillespie, III, Athens, TX (US); Doug Owen Crow, Brownsboro, TX (US)

(73) Assignee: West Pharmaceutical Services, Inc., Lionville, PA (US)

( * ) Notice: Subject to any disclaimer, the term of this patent is extended or adjusted under 35 U.S.C. 154(b) by 0 days.

(21) Appl. No.: 12/749,836

(22) Filed: Mar. 30, 2010

(65) Prior Publication Data

US 2010/0185148 A1  Jul. 22, 2010

Related U.S. Application Data

(63) Continuation-in-part of application No. 12/530,539, filed as application No. PCT/US2009/047483 on Jun. 16, 2009.

(60) Provisional application No. 61/074,253, filed on Jun. 20, 2008.

(51) Int. Cl.
A61M 5/00 (2006.01)
A61M 5/32 (2006.01)

(52) U.S. Cl. .................................... 604/110; 604/197

(58) Field of Classification Search .................. 604/110, 604/135, 134, 136, 263, 111
See application file for complete search history.

(56) References Cited

U.S. PATENT DOCUMENTS

| | | | |
|---|---|---|---|
| 4,640,686 A | 2/1987 | Dalling et al. | |
| 5,451,210 A | 9/1995 | Kramer et al. | |
| 5,843,036 A | 12/1998 | Olive et al. | |
| 6,210,369 B1 | 4/2001 | Wilmot et al. | |
| 6,428,528 B2 | 8/2002 | Sadowski et al. | |
| 6,565,553 B2 | 5/2003 | Sadowski et al. | |
| 6,986,760 B2 | 1/2006 | Giambattista et al. | |
| 7,011,649 B2 | 3/2006 | De La Serna et al. | |
| 7,066,907 B2 | 6/2006 | Crossman et al. | |
| 7,297,136 B2 | 11/2007 | Wyrick | |
| 7,314,464 B2 | 1/2008 | Giambattista et al. | |
| 2004/0039336 A1 | 2/2004 | Amark et al. | |
| 2004/0193110 A1 | 9/2004 | Giambattista et al. | |
| 2005/0113750 A1 | 5/2005 | Targell | |
| 2005/0283115 A1 | 12/2005 | Giambattista et al. | |
| 2005/0288633 A1 | 12/2005 | Jeffrey | |
| 2006/0270986 A1 | 11/2006 | Hommann et al. | |
| 2007/0129686 A1 | 6/2007 | Daily et al. | |
| 2007/0135767 A1* | 6/2007 | Gillespie et al. ............... 604/135 |
| 2007/0173770 A1* | 7/2007 | Stamp ............................ 604/187 |
| 2007/0265568 A1* | 11/2007 | Tsals et al. ..................... 604/136 |
| 2007/0293819 A1 | 12/2007 | Giambattista et al. | |
| 2008/0132838 A1 | 6/2008 | Wyrick | |
| 2008/0228143 A1 | 9/2008 | Stamp | |
| 2009/0005737 A1 | 1/2009 | Chun | |
| 2009/0054849 A1 | 2/2009 | Burnell et al. | |
| 2010/0152655 A1 | 6/2010 | Stamp | |

* cited by examiner

OTHER PUBLICATIONS

International Search Report and Written Opinion for the related International Patent Application No. PCT/US2009/047483 dated Jul. 23, 2009.

*Primary Examiner* — Nicholas Lucchesi
*Assistant Examiner* — Jenna Zhang
(74) *Attorney, Agent, or Firm* — Panitch Schwarze Belisario & Nadel LLP

(57) ABSTRACT

The present invention provides an injector apparatus suitable for use with an automatic injection device. The injector apparatus includes a cylindrical housing having a deflectable member and a removable guard. The deflectable member releasably holds a syringe tube assembly in the axial direction when the apparatus is in the initial position. Then, after use, the deflectable member provides a tamper evidence means for indicating whether or not the injector apparatus was previously used or tampered with.

23 Claims, 17 Drawing Sheets

INJECTOR APPARATUS

CROSS-REFERENCE TO RELATED APPLICATIONS

The present application is a continuation-in-part of U.S. patent application Ser. No. 12/530,539 filed Sep. 9, 2009, which is a Section 371 of International Application No. PCT/US2009/047483, filed Jun. 16, 2009, and which claims the benefit of priority pursuant to 35 U.S.C. §119(e) of U.S. Provisional Patent Application No. 61/074,253, filed Jun. 20, 2008, the disclosures of which are hereby incorporated herein by reference in their entirety.

BACKGROUND OF THE INVENTION

The present invention relates to automatic injection devices ("autoinjectors"). In particular, the present invention relates to an autoinjector having an automatically deployable frontal buttress.

Autoinjector mechanisms have commercially been developed to substitute an automated mechanism for the manual action of inserting a hypodermic needle into a recipient's flesh and forcing the medicament out of the syringe, through the hypodermic needle and into the recipient. In some cases, the automated mechanisms are designed to utilize commercially commonplace pre-filled syringes. The pre-filled syringes are typically manufactured by pharmaceutical companies, or in some cases a third party. The manufacturers thereafter assemble the pre-filled syringes into autoinjectors for commercial distribution. Examples of such devices include the EpiPen® manufactured by Meridian Medical Technologies, Inc., of Bristol, Tenn., the Humira® manufactured by Owen Mumford Ltd., of Oxford, United Kingdom, and the SureClick® system marketed by Scandinavian Health Limited, of Florham Park, N.J. Autoinjectors have proven to be beneficial for patients exhibiting psychological paranoia of receiving parenteral injections (e.g., needle phobic individuals and young children) and/or those without the manual dexterity or clear eyesight necessary to self-administer injections using conventional syringes.

Conventional autoinjectors generally provide a compression spring-based mechanism to drive the syringe in the distal direction within a housing (the housing contains the syringe) and some means to initiate the automatic injection process. When triggered, the compressed spring is released from end-to-end confinement. Typically, the spring is confined to abut against an interior surface of the housing about its proximal end such that releasing the compressed spring causes axial extension in the distal direction. The spring, typically acting through one or more surrogate components, impinges upon the syringe, and/or an elastomeric piston element thereof, causing the syringe to translate in the distal direction until the hypodermic needle associated with the syringe extends beyond the distal end of the housing.

The extended length of the needle determines the depth of drug delivery at the injection site. The exposed length of the needle (i.e., that portion of the needle exterior to the autoinjector housing at needle extension) is known as the "needle insertion depth." The correlation between extended length and insertion depth assumes that the distal end of the autoinjector is pressed against the injection site during autoinjector actuation. In most therapeutic applications, it is important that the depth of needle insertion be accurately controlled to assure the drug is delivered into a specific tissue mass, for example the subcutaneous tissue residing between the dermal skin layer and the musculature. Known and repeatable depth of needle insertion is therefore a desirable attribute of autoinjector devices.

Billions of pre-filled syringes of borosilicate glass as described above are manufactured on an annual basis. The proximal end of the glass syringe is formed into a radially disposed, disk-shaped flange. The flange may thereafter be cut on two sides in parallel planes in close proximity to the syringe body to form oblong and opposing finger grips. This glass syringe configuration is know as a cut-flange configuration. Glass syringes, and more particularly cut flange syringes, represent a number of challenges in autoinjector applications because they are fragile and include easily broken components with a relatively high degree of dimensional variability. The high degree of dimensional variability leads to variability in the exposed length of the hypodermic needle beyond the distal end of the glass syringe and the overall length of the syringe. In addition, the cut flanges of such glass syringes have varying degrees of irregularity and asymmetry with respect to a central axis along the center of the syringe barrel and a plane perpendicular to the central axis.

Conventional autoinjectors are configured to stop the forward movement of the syringe at a desired forward position at the end of needle insertion based off of the syringe flange. That is, the syringe flange becomes a de facto point of registration, in other words a datum surface, which dictates the relative axial relationship between the syringe features and the other elements of the auto-injector. Under such configurations, any variability, whether associated with the overall length of the syringe, length of the exposed needle, or variability associated with the syringe flange itself, translates directly into variability in the extended needle length and needle insertion length. In addition, due to the abrupt deceleration of the syringe/carrier assembly at the end of needle insertion, impact loads are imposed on the fragile syringe flanges. In other words, the force applied by the autoinjector in driving the syringe distally creates an opposing force imposed on the syringe flange by its registration point of contact. In addition, a bending moment is borne by the flange as a result of the radial distance between the centerline of the piston and the flange. The bending moment increases the stress applied to the fragile flange increasing the risk of fracture.

Moreover, conventional autoinjectors are typically configured with a fixed stroke length. That is, conventional autoinjectors are designed to drive the plunger of the syringe a fixed distance from some fixed reference point on the autoinjector. Thus, with increased variability in the overall length of the glass syringe used in such autoinjectors, the fixed stroke length results in increased variability of residual medicament volume after injection. Such variability in residual medicament volume translates into significant monetary waste due to the relatively high cost of the drugs used to manufacture the medicaments.

Thus, conventional autoinjectors are deficient in that they cannot accommodate conventional pre-filled glass syringes (i.e., staked-needed syringes) to effectively address the issues associated with fragile and irregular components while assuring accurate needle placement and precise dose delivery due to the dimensional variability of glass syringe manufacturing. As such, there is still a need for an autoinjector that can provide accurate needle insertion depth and precise dose delivery using a pre-filled glass syringe.

In addition, conventional pre-filled glass syringes are typically supplied as an assembly with a needle shield that includes an elastomeric element to provide a means to sealably encapsulate the hypodermic needle. FIG. 2A illustrates a conventional pre-filled glass syringe 46 having a barrel 51. The needle shield 60 serves as a sterility barrier for the needle 61 (FIG. 2B) and its fluid contents as the syringe 46 is pre-sterilized at the factory. Once delivered to the pharmaceutical company, the syringe 46 is filled with medicament within a sterile filling suite. Often, the needle shield 60 is itself encapsulated with a rigid component to provide additional protection against needle damage and to provide a suitable means to manually remove the needle shield 60. Thus, the needle shield 60 is commonly know as a rigid needle shield ("RNS"). In such RNSs, an open end allows access to the elastomeric interior through which the needle 61 is introduced into the elastomeric interior. The RNS is removably attached to the syringe 46 by a circumferential compression fit between the compliant elastomeric element of the RNS and cooperative features present on the distal end of the syringe 46. In addition, such RNSs have an overall outer diameter that is approximately the same as that of the syringe 46.

Such conventional syringes 46 can be used as a stand alone manually operable syringe 46 or in combination with a suitable autoinjector. Such autoinjectors are provided with a means to remove the RNS 60 before administering the injection. This is typically accomplished by a component provided as part of the autoinjector that engages the needle shield 60 during final assembly and provides a graspable handle with which a user can grasp to extract the needle shield 60 in the axial, distal direction. However, the use of such handles to disengage the RNS 60 creates an annular void or open end about the distal end of the autoinjector. Moreover, as the handle to remove the RNS 60 occupies space at the distal end on the autoinjector, this precludes the use of such space for any potential buttress surface upon which the syringe 46 may engage.

Consequently, an autoinjector that is capable of accommodating a glass, cut flange syringe 46 with a RNS 60 attached would present pharmaceutical companies with a significant advantage in being able to provide one primary pre-filled syringe that can be used either in a manual setting or, alternatively, in conjunction with an autoinjector.

The present invention also relates to an injector apparatus that provides a means to resist recapping the injector apparatus or for securely encapsulating a spent injector apparatus with a guard. Such resistance means also provides to a user an indication of whether or not the injector apparatus has been used or tampered with.

BRIEF SUMMARY OF THE INVENTION

In a preferred embodiment, the present invention comprises a cylindrical housing, a tubular syringe guide, a biasing member, and a guard. The cylindrical housing includes a deflectable member having a radially outward protrusion and a radially inward protrusion. The tubular syringe guide is housed within the cylindrical housing to receive a barrel of a syringe. The syringe guide includes a tubular body, a recess about a proximal end of the tubular body, and a radially outwardly extending flange about a distal end of the tubular body. The biasing member includes a first end that engages the radially outwardly extending flange, and a second end that engages a distal end of the housing. The guard is releasably connected to the distal end of the housing. The guard includes a tubular guard body to receive the deflectable member and the syringe guide. The deflectable member is movable between a biased inward position with the radially inward protrusion residing within the recess of the syringe guide and between the syringe guide and the guard to releasably hold the syringe guide from moving in an axial direction, and a biased outward position when the guard is removed from the housing such that the radially inward protrusion engages an exterior surface of the tubular body spaced apart from the recess. When in the outward position, the radially outward protrusion extends beyond an exterior surface of the cylindrical housing to impede the guard from being fully reseated on the housing.

In another preferred embodiment, the present invention comprises a cylindrical housing, a tubular syringe guide, and a guard. The cylindrical housing includes a proximal housing and a distal housing. The proximal housing has a transverse surface, and an opening through the transverse surface for the passage of a plunger rod. The distal housing is connected to the proximal housing and includes a plurality of deflectable members distal to the proximal housing. Each deflectable member includes a radially outward protrusion and a radially inward protrusion. The tubular syringe guide is housed within the distal housing to receive a syringe body and is slidable relative to the distal housing. The syringe guide includes a tubular body, a recess about a proximal end of the tubular body, and a distal end that engages a biasing member to slide the syringe guide in the proximal direction relative to the distal housing. The guard is releasably connected to the distal housing and includes a tubular guard body to receive the plurality of deflectable members. Each deflectable member is movable between a biased inward position with each radially inward protrusion residing within the recess of the syringe guide and between the syringe guide and the guard to releasably hold the syringe guide from moving in an axial direction, and a biased outward position in which each radially inward protrusion engages an exterior surface of the tubular body spaced apart from the recess. The radially outward protrusion extends beyond an exterior surface of the distal housing when the guard is removed from the distal housing to impede the guard from being fully reseated on the housing.

In yet another preferred embodiment, the present invention comprises a cylindrical housing, a tubular sleeve, a tubular syringe guide and a guard. The cylindrical housing includes a transverse surface internal to the cylindrical housing and an aperture along a side wall of the housing distal to the transverse surface. The transverse surface has an opening for the passage of a plunger rod therethrough. The tubular sleeve is connected to and housed within the cylindrical housing distal to the transverse surface. The tubular sleeve includes a deflectable member. The tubular syringe guide is housed within the tubular sleeve to receive a syringe body and is slidable relative to the tubular sleeve. The syringe guide has a proximal end having a recess, and a distal end that engages a biasing member to slide the syringe guide in the proximal direction relative to the tubular sleeve. The guard is releasably connected to the cylindrical housing and includes a tubular guard body to receive a distal end of the cylindrical housing and the deflectable member. The deflectable member includes a radially inward protrusion that resides within the recess of the syringe guide, and a radially outward protrusion that extends through the aperture of the cylindrical housing and directly engages an interior surface of the guard to releasably hold the syringe guide from moving in an axial direction.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
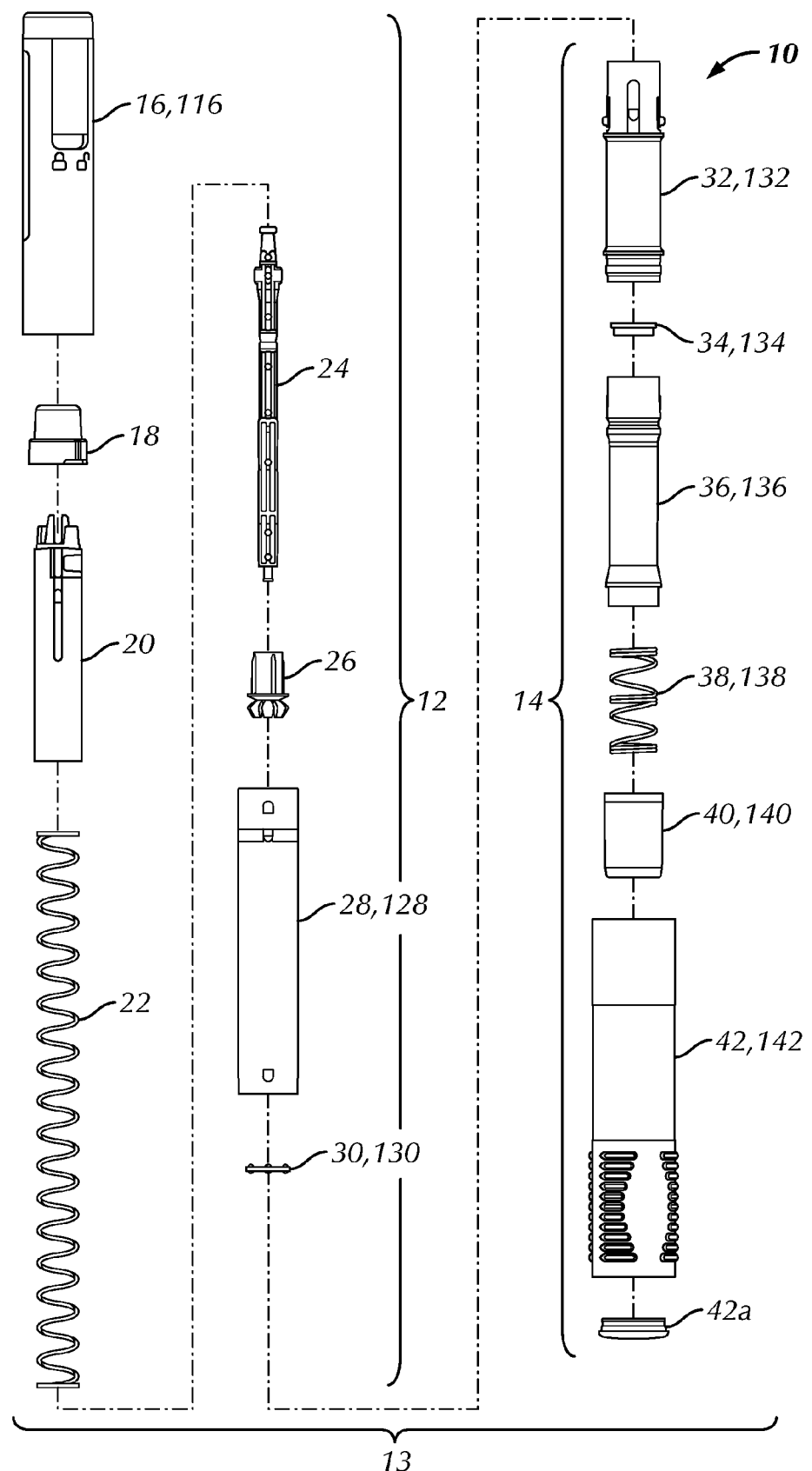
FIG. 1 is an exploded elevational view of the window tube subassembly and injection assembly of an autoinjector in accordance with a preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the identified element and designated parts thereof. Additionally, the term "a," as used in the specification, means "at least one." The terminology includes the words noted above, derivatives thereof and words of similar import.

In a preferred embodiment, the present invention provides for an automatic injection device that includes an automatically deployable buttress upon which a syringe can be registered.

As shown in FIGS. 1, 3, 6 and 7, the autoinjector 10 includes a housing 13 generally formed by various components of an injection assembly (or power pack subassembly) 12 and a window tube subassembly 14, such as an inner housing 20, a mid housing 28, a window tube 32 and a nose 40. While the present embodiment preferably includes an injection assembly 12, it is within the intent and scope of the present invention, that any injection assembly capable of automatically deploying or of causing a syringe to be automatically injected, can be used. For example, exemplary automatic injection devices applicable to the present invention include those disclosed in U.S. Pat. No. 6,387,078 to Gillespie, III, the disclosure of which is hereby incorporated by reference in its entirety. In general, the autoinjector 10 is configured to be a modular autoinjector 10 in which the injection assembly 12 and window tube subassembly 14 can be readily assembled with a conventional syringe 46 at the time of use. Such conventional syringes can also include plastic syringes and cartridge based syringes.

Figure 3:
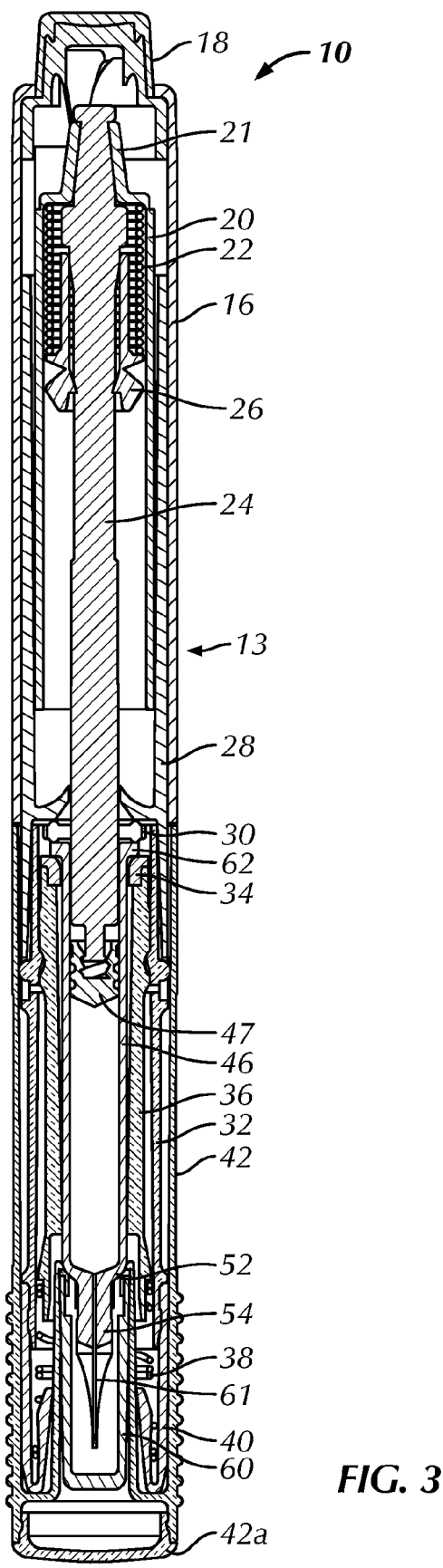
FIG. 3 is a cross-sectional elevational view of an autoinjector in accordance with the preferred embodiment of the present invention in a fully assembled state.
Figures 6, 7:
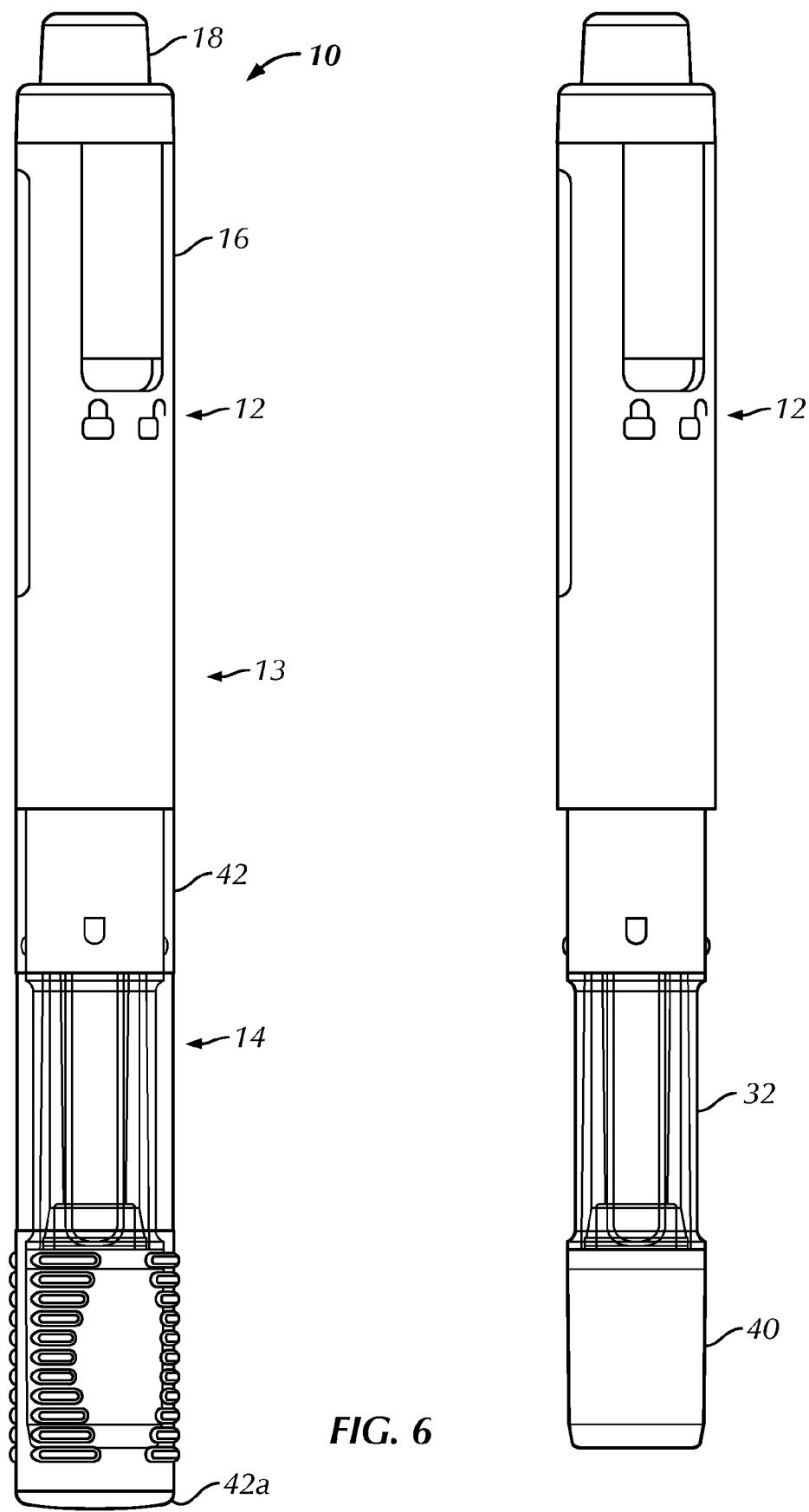
FIG. 6 is a side elevational view of the autoinjector of FIG. 3.
FIG. 7 is a side elevational view of the autoinjector of FIG. 6 with the handle removed.

Preferably the injection assembly 12 includes a cap 16, an activation button 18, an inner housing 20, an injection spring 22, a plunger rod 24, a piston 47, a spring rest 26, a mid housing 28 and an optional syringe ring 30, as best shown in FIGS. 1 and 3. FIGS. 3 and 6 illustrate the injection assembly 12 in an assembled ready-to-use state and assembled to the window tube subassembly 14. As described hereinafter, distal refers to toward the needle-end of the autoinjector 10 and proximal refers to toward the button-end of the autoinjector 10.

In an assembled state, the spring rest 26 is releasably connected to about the middle of the plunger rod 24 by cooperating detents. The plunger rod 24 and spring rest 26 are positioned within the inner housing 20 with the injection spring 22 in between the proximal end of the inner housing 20 and an outer surface of the spring rest 26. The injection spring 22 is maintained in a compressed state by catches 21 on the inner housing 20 that retain the proximal head of the plunger rod 24. The activation button 18 is positioned on top of the proximal end of the inner housing 20 and the cap 16 and functions to release the catches 21 to release the spring 22 upon depression. The foregoing assembly resides within the mid housing 28 and cap 16.

Figure 2A:
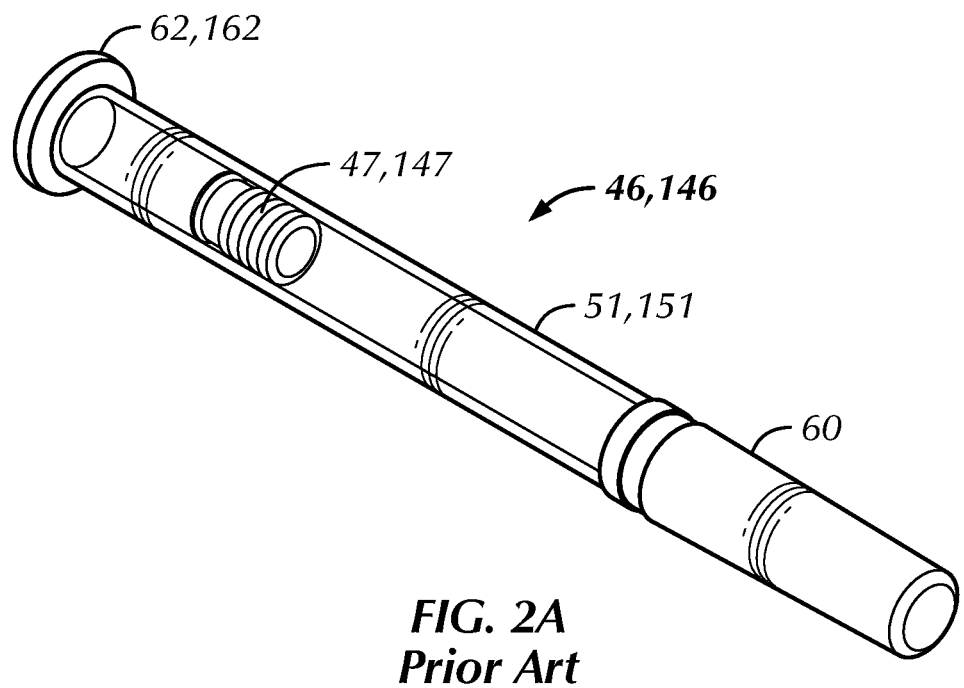
FIG. 2A is a perspective view of a conventional glass syringe with a rigid needle shield applicable for use within the autoinjector of FIG. 1.

Referring back to FIG. 1, the window tube subassembly 14 includes a window tube 32, a syringe cushion 34, a syringe guide 36, a return spring 38, a nose 40, a handle 42 and a handle cap 42a. FIG. 3 illustrates the syringe 46 housed within the housing 13. The syringe 46 includes a barrel 51 and a shoulder 52 about a distal end of the barrel 51 (FIG. 2A). FIGS. 3 and 6 illustrate the window tube subassembly 14 in an assembled ready-to use state and assembled with the injection assembly 12.

The syringe guide 36 is housed within the housing 13, is generally cylindrical in shape, and is configured to receive the barrel 51 of a syringe 46. When assembled with the syringe 46, the flange 62 of the syringe 46 rests upon the cushion 34 and the proximal end of the syringe guide 36 (see FIG. 3) and the nose 54 of the syringe 46 extends partially beyond the distal end of the syringe guide 36 (see FIGS. 3 and 4A). As a result, the syringe 46 moves in tandem with the syringe guide 36 upon the distal movement of the syringe guide 36.

Figure 4A:
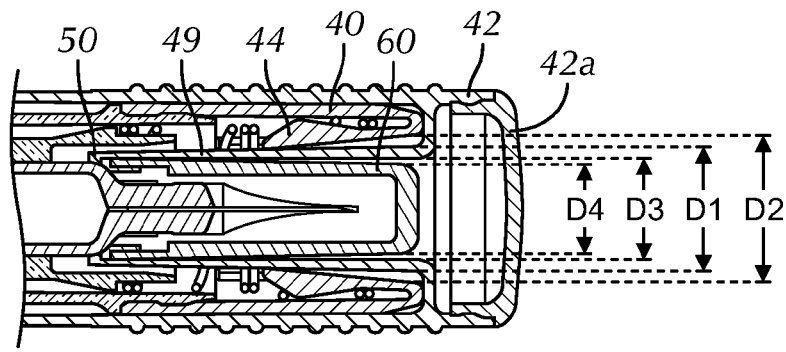
FIG. 4A is an enlarged cross-sectional elevational view of the distal end of the autoinjector of FIG. 3 with a handle in a fully assembled position.

The handle 42 (as shown in FIGS. 1, 3, 4A-C, 6, 8 and 9) is releasably connected to the distal end of the housing 13. The handle 42 includes a body 63 that is generally cylindrical in shape and configured to receive the assembly of the window tube 32, syringe cushion 34, syringe 46, syringe guide 36, return spring 38 and nose 40. The distal end of the handle 42 is also configured with a needle shield remover 49 (FIG. 9) having a generally cylindrical body 65 and latches 50 at the most proximal end of the needle shield remover 49. The needle shield remover 49 is integrally formed and connected to the distal end of the handle 42. Alternatively, the needle shield remover 49 can be a separate component secured to the handle 42. The needle shield remover 49 is configured to be received within the nose 40 and over the needle shield 60. That is, the needle shield remover 49 is sized with an outside diameter (D1) that is at least slightly smaller than the inside diameter (D2) of the flexible members 44 when in the fully opened position and an inside diameter (D3) that is at least slightly greater than the outside diameter (D4) of the needle shield 60, as best shown in FIG. 4A. Thus, the needle shield remover 49 is configured to maintain the plurality of radially disposed circumferentially spaced flexible members 44 in the first position (i.e., open position), as shown in FIG. 4A.

The latches 50 (FIG. 9) can be configured as a radially inwardly disposed flange which engages the proximal end of the needle shield 60. As a result, when the handle 42 is removed, the latches 50 engage the needle shield 60 to thereby also remove the needle shield 60 from the syringe 46. In addition, the latches 50 are preferably configured with a chamfered proximal surface to provide ease of assembly over the needle shield 60.

Figure 2B:
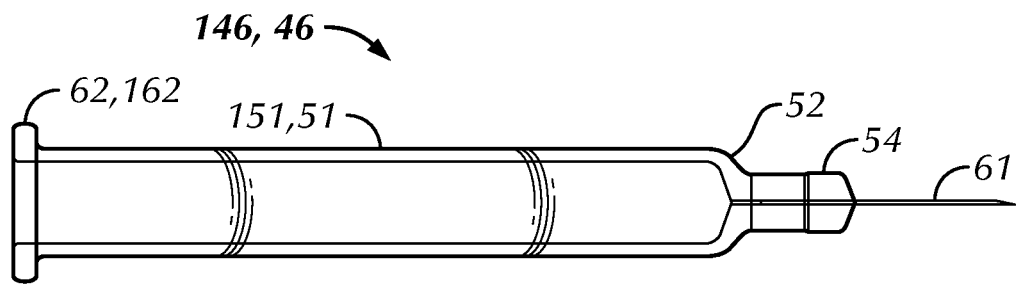
FIG. 2B is a partial side cross-sectional view of the syringe of FIG. 2A without the rigid needle shield.
Figure 5A:
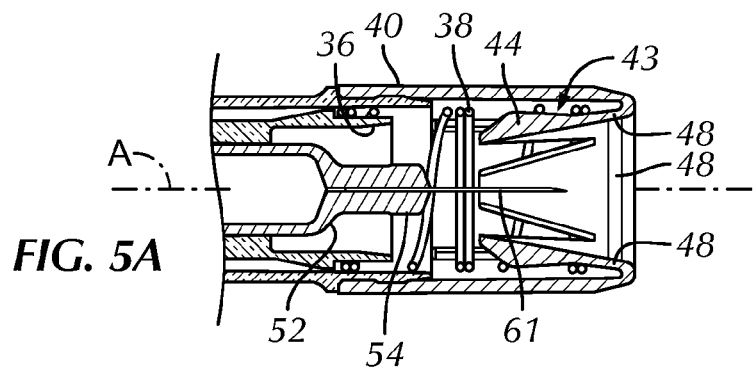
FIG. 5A is an enlarged cross-sectional elevational view of the distal end of the autoinjector of FIG. 3 with the handle completely removed and in a pre-activation state.
Figure 5B:
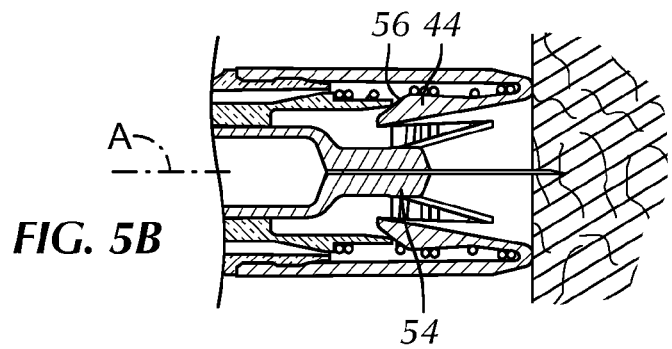
FIG. 5B is an enlarged cross-sectional elevational view of the distal end of the autoinjector of FIG. 3 with a syringe guide initially engaging flexible members of a frontal buttress.
Figure 5C:
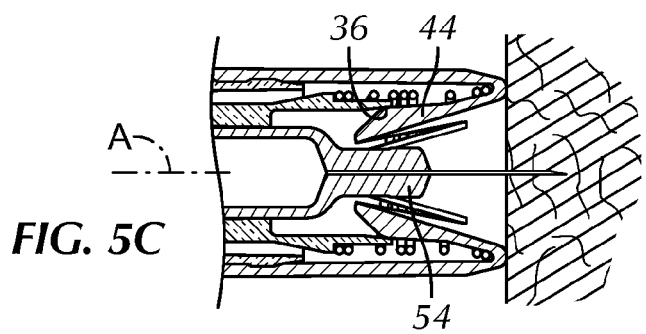
FIG. 5C is an enlarged cross-sectional elevational view of the distal end of the autoinjector of FIG. 3 with the syringe guide engaging an outer surface of the flexible members of the frontal buttress.
Figure 5D:
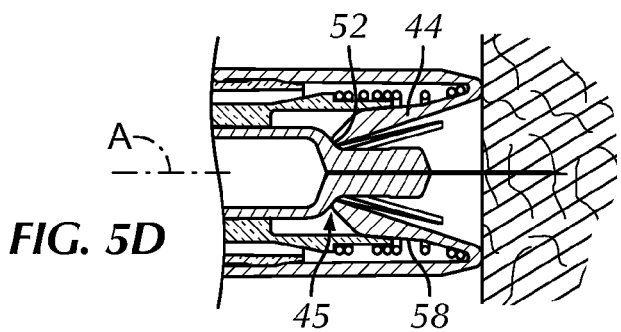
FIG. 5D is an enlarged cross-sectional view of the distal end of the autoinjector of FIG. 3 with a shoulder of the syringe engaging a buttress surface formed by the frontal buttress.

In an assembled state, as shown in FIG. 3, the handle cap 42a is secured to the handle 42 and the nose 40 is assembled to the window tube 32. The return spring 38 seats within the nose 40 and the syringe guide 36 resides on top of the return spring 38 with the syringe cushion 34 residing on the syringe guide 36. The return spring 38, syringe guide 36 and syringe cushion 34 reside within the window tube 32, which mates with the nose 40. A syringe 46 (e.g., a pre-filled glass syringe, as shown in FIGS. 2A and 2B) is inserted into the syringe guide 36 such that the syringe ring 30 rests upon a proximal edge of the flange 62 of the syringe 46 and the plunger rod 24 is inserted within the barrel of the syringe 46. The syringe 46 is maintained in radial confinement within the syringe guide 36 by a running annular fit between the exterior of the syringe 46 and the interior bore of the syringe guide 36. The syringe 46 is maintained in axial relation to the syringe guide 36 by force applied to the proximal end of the syringe 46 by the injection spring 22 acting upon the syringe 46 through one or more components. As such, the syringe 46 and syringe guide 36 travel in tandem upon activation until the syringe 46 engages a buttress surface 45 formed by a frontal buttress 43, as shown in FIG. 5D.

To activate the injection assembly 12, a user removes the handle 42, and presses the nose 40 against the injection site and depresses activation button 18, thereby causing the plunger rod 24 to disengage from the inner housing 20. Upon disengagement of the plunger rod 24, the injection spring 22, which is initially in the compressed state, expands to exert a driving force on the spring rest 26 that is connected to the plunger rod 24, which subsequently causes the syringe 46 to move distally. In sum, the injection assembly 12 is operatively connected to the syringe 46 and configured to bias the syringe 46 from an initial position (FIG. 4A) in which the syringe 46 is shrouded by the housing 13 to an extended position (FIG. 5D) in which a portion of the syringe 46 extends beyond the housing 13.

FIGS. 5A-D, 9 and 10 illustrate a frontal buttress 43 connected to a distal end of the housing 13. The frontal buttress 43 includes a plurality of radially disposed circumferentially spaced flexible members 44. The flexible members 44 are generally configured in a pyramidal-like shape such that when in the closed position (see FIG. 5D) the flexible members 44 form a generally frustroconical shape with the smaller diameter section proximal to the larger diameter section. Preferably, the radially disposed circumferentially spaced flexible members 44 are located on an interior of the housing 13 and extend proximally from the distal end of the housing 13 such that the flexible members 44 collectively form a buttress surface 45 that engages the shoulder 52 of the syringe 42.

Figure 11:
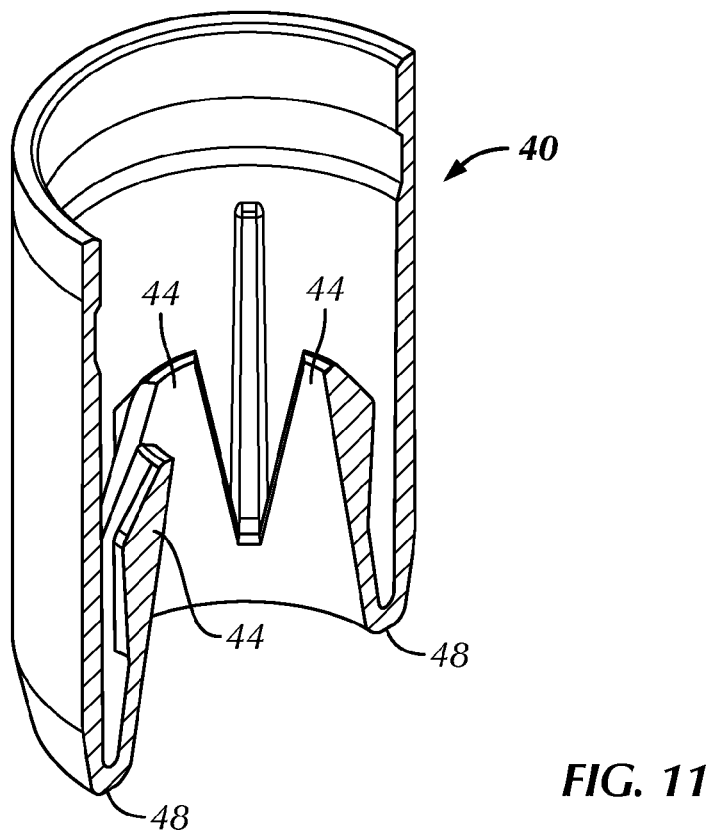
FIG. 11 is a cross-sectional perspective view of the nose of FIG. 10.

In the present embodiment, the nose 40 is configured to include the frontal buttress 43. The bases 48 of each of the flexible members 44 are connected to the nose 40 along the interior distal end of the nose 40, as best shown in FIGS. 5A and 11. The connection of the flexible members 44 to the nose 40 is configured as a flexible connection such that the flexible members 44 can flex between a first open or spread apart position/state (as shown in FIG. 4A) and a second closed, closer together position/state (as shown in FIG. 5D). The flexible members 44 are also configured to be biased toward the closed position. The biasing force results from the flexible members 44 initially being molded and configured to be in the closed position and then being forced into the open position by the handle 42. As a result, due to the tensile properties of the frontal buttress 43, the flexible members 44 maintain a radially inward bias. That is, the flexible members 44 flex radially inwardly when in the closed state.

In sum, the frontal buttress 43 is configured to move from a first open position (FIG. 4A) when the syringe 46 is in the initial position to a second closed position (FIG. 5D) to engage the shoulder 52 of the syringe 46 when in the extended position. The flexible members 44 can be made from any polymer, such as a rigid plastic or thermoplastic elastomer. Preferably, the flexible members 44 are made from a polyacetal or a thermoplastic elastomer.

Figure 4B:
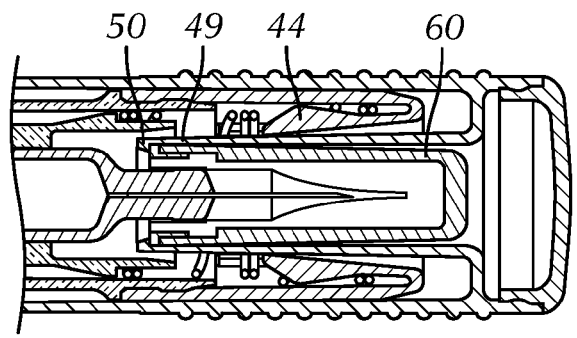
FIG. 4B is an enlarged cross-sectional elevational view of the distal end of the autoinjector of FIG. 3 with the handle in a partially removed position.
Figure 4C:
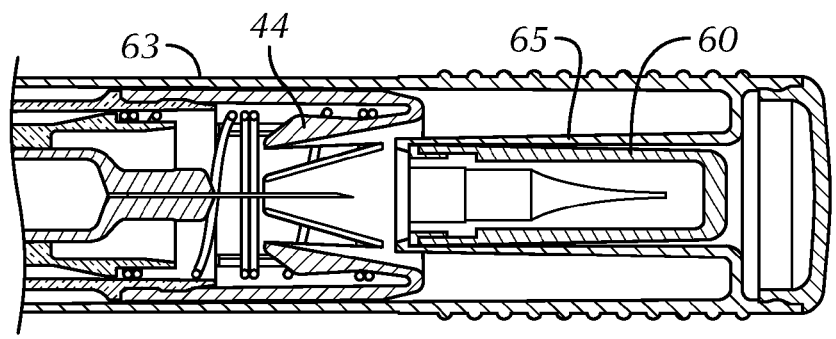
FIG. 4C is an enlarged cross-sectional elevational view of the distal end of the autoinjector of FIG. 3 with the handle in a further partially removed position.

As shown in FIGS. 4A-C, the nose 40 is assembled with the handle 42. In the fully assembled state, the handle 42 is fully inserted onto the nose 40 such that the shield remover 49 of the handle 42 forces the flexible members 44 into the open position (FIG. 4A). FIGS. 4B and 4C illustrate various stages of removal of the handle 42 from the autoinjector 10. As best shown in FIGS. 4B and 4C, as the handle 42 is removed, the latches 50 of the needle shield remover 49 simultaneously remove the needle shield 60. After the handle 42 is removed, the bias of the flexible members 44 causes the flexible members 44 to initially move toward a centerline (A), flexing at the base 48, thereby reorienting the proximal ends of the flexible members 44 to a position within the inside diameter of the syringe guide 36 (i.e., a pre-activation or ready-to-use state, as shown in FIG. 5A).

After the handle 42 is removed and upon activation of the autoinjector 10, the injection assembly 12 forces the syringe guide 36/syringe 46 assembly to engage the frontal buttress 43. As shown in FIGS. 5A-5D, as the syringe guide 36/syringe 46 assembly moves distally, a distal edge of the syringe guide 36 engage an outside surface of the flexible members 44. Preferably, the outside surface of the flexible member 44 includes a chamfered or inclined surface 56 that slopes radially inwardly. Upon continued distal movement of the syringe guide 36/syringe 46 assembly, the distal edge of the syringe guide 36 slidingly engages the flexible members 44 causing the flexible members 44 to collectively deflect inwardly toward the centerline (A) of the autoinjector (FIG. 5D). Preferably, the syringe guide 36/syringe 46 assembly is configured such that the nose 54 of the syringe 46 initiates passage through the nose 40 of the autoinjector 10 prior to the flexible members 44 completely flexing inwardly. Upon full deployment of the syringe 46, by the radial confinement and column strength of the flexible members 44, the proximal ends of the flexible members 44 advantageously provide for an effective buttress surface 45 to the shoulder 52 of the syringe 46. Moreover, at the end of needle insertion and once the syringe 46 abuts against the buttress surface 45 (as shown in FIG. 5D) the syringe 46 remains in contact with the buttress surface 45 while liquid medicament is forced out of the syringe 46 and into the injection site.

Preferably, the flexible members 44 are also configured with a planar outside surface 58 that is oriented substantially parallel to the centerline (A) when the flexible members 44 are in the closed position, as best shown in FIG. 5D. The substantially parallel outside surface 58 advantageously allows for sliding engagement (or play) between the flexible members 44 and the syringe guide 36, such that the syringe guide 36 can accommodate a wide range of variability in the overall length of the syringe 46 and still function to close the flexible members 44 without bottoming out at the base 48 of the frontal buttress 43. Moreover, the sliding relationship assures engagement of the frontal buttress 43 by the syringe 46 without risk of stressing the syringe flange 62.

In sum, the present invention advantageously provides for an autoinjector that can accommodate a conventional syringe (such as a pre-filled glass syringe) and provide a robust means to automatically stop forward (i.e., distal) movement and provide a more consistent and accurate frontal position during needle insertion (i.e., needle insertion depth) and dose delivery, respectively, by registering the stop of needle depth insertion upon the shoulder 52 of the syringe 46 rather than the flange 62. By eliminating the load on the syringe flange 62, the risk of syringe flange fracture is also significantly reduced. Moreover, the accuracy of dose delivery and reduction in residual fluid volume within the syringe post-injection is significantly enhanced, thus saving considerable costs associated with manufacturing pre-filled syringes. The present invention also advantageously provides for an autoinjector having an automatically deployable frontal buttress 43 such that the forward end of the syringe 46 becomes the load bearing or datum surface, thereby reducing stress on the syringe flange 62 and reducing variability in needle insertion depth by eliminating the variability associated with overall length and flange dimensions of glass syringes.

In addition, as the present invention is configured for use with conventional pre-filled syringes, such as glass staked-needle syringes, plastic syringes, and cartridge based syringes with needle hubs, there is no need for any additional sterilization of the autoinjector after assembly with the pre-filled syringe as the medicament within the pre-filled syringe is maintained within a sterile environment regardless of the sterility of the autoinjector. This helps reduce the overall costs associated with autoinjector manufacturing. In addition, because of the modular configuration of the present invention, it allows for pre-filled syringes to be assembled and prepared at one location and the autoinjector components to be prepared at a separate location and/or at different times, thus allowing for greater manufacturing versatility. Moreover, as the autoinjector of the present invention can be assembled with conventional pre-filled syringe at the time of use, the two devices are not constrained to a single expiration date of the device. Thus, the usability or shelf life of the autoinjector will not depend upon the expiration date of the pre-filled syringe.

Figure 12:
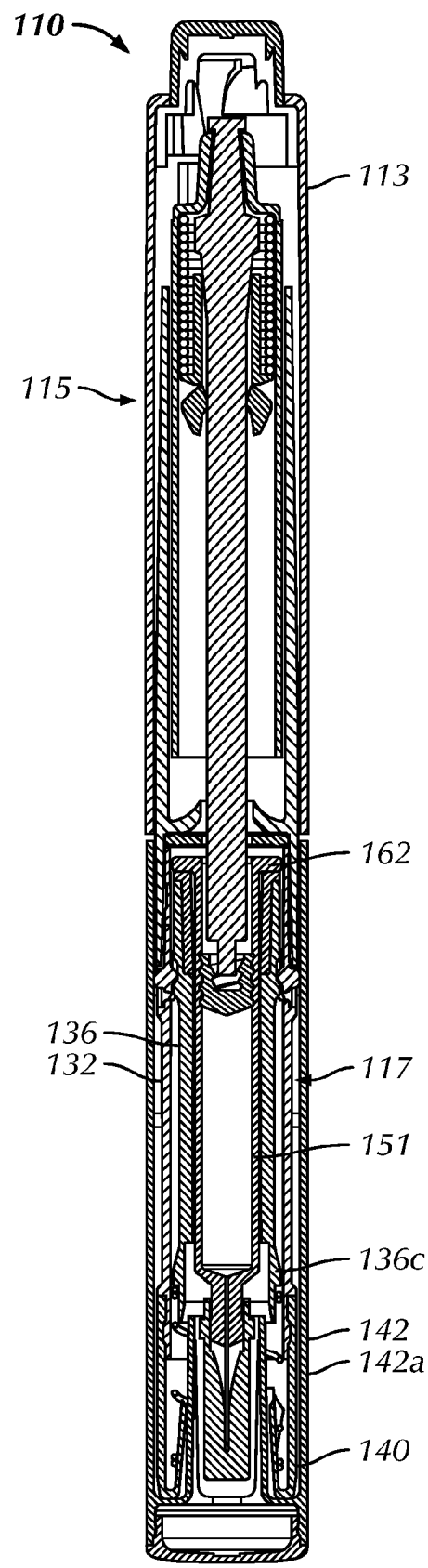
FIG. 12 is a cross-sectional elevational view of an injector apparatus in accordance with another aspect of the present invention in a fully assembled state.
Figure 13:
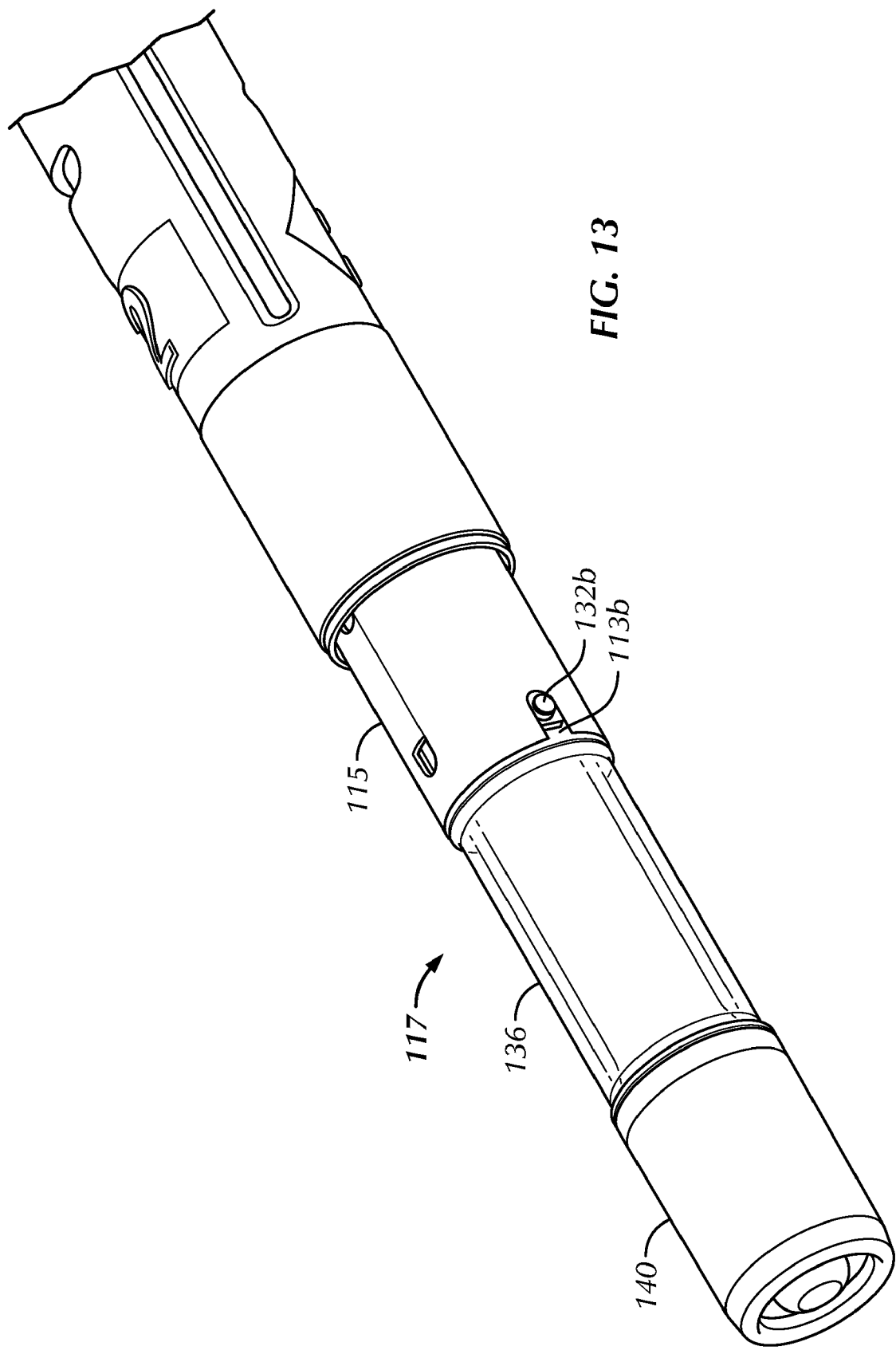
FIG. 13 is a perspective view of the injector apparatus of FIG. 12 without a guard.

Another aspect for the present invention is shown in FIGS. 1, 2A, 2B, 8, 9 and 12-19. In particular, this aspect of the present invention provides for an injector apparatus 110 that includes a cylindrical housing 113, a tubular syringe guide 136 and a guard 142 (also referred to as a handle in the above embodiment), as best shown in FIG. 12. The cylindrical housing 113 includes a proximal housing 115 and a distal housing 117 connected to the proximal housing 115. The proximal housing includes a cap 116 and a mid housing 128 (FIG. 1). The mid housing 128 is assembled within the cap 116, as further described above for the mid housing 28 and cap 16. Collectively, the mid housing 128 and cap 116 form, in part, the proximal housing 115.

Figure 15:
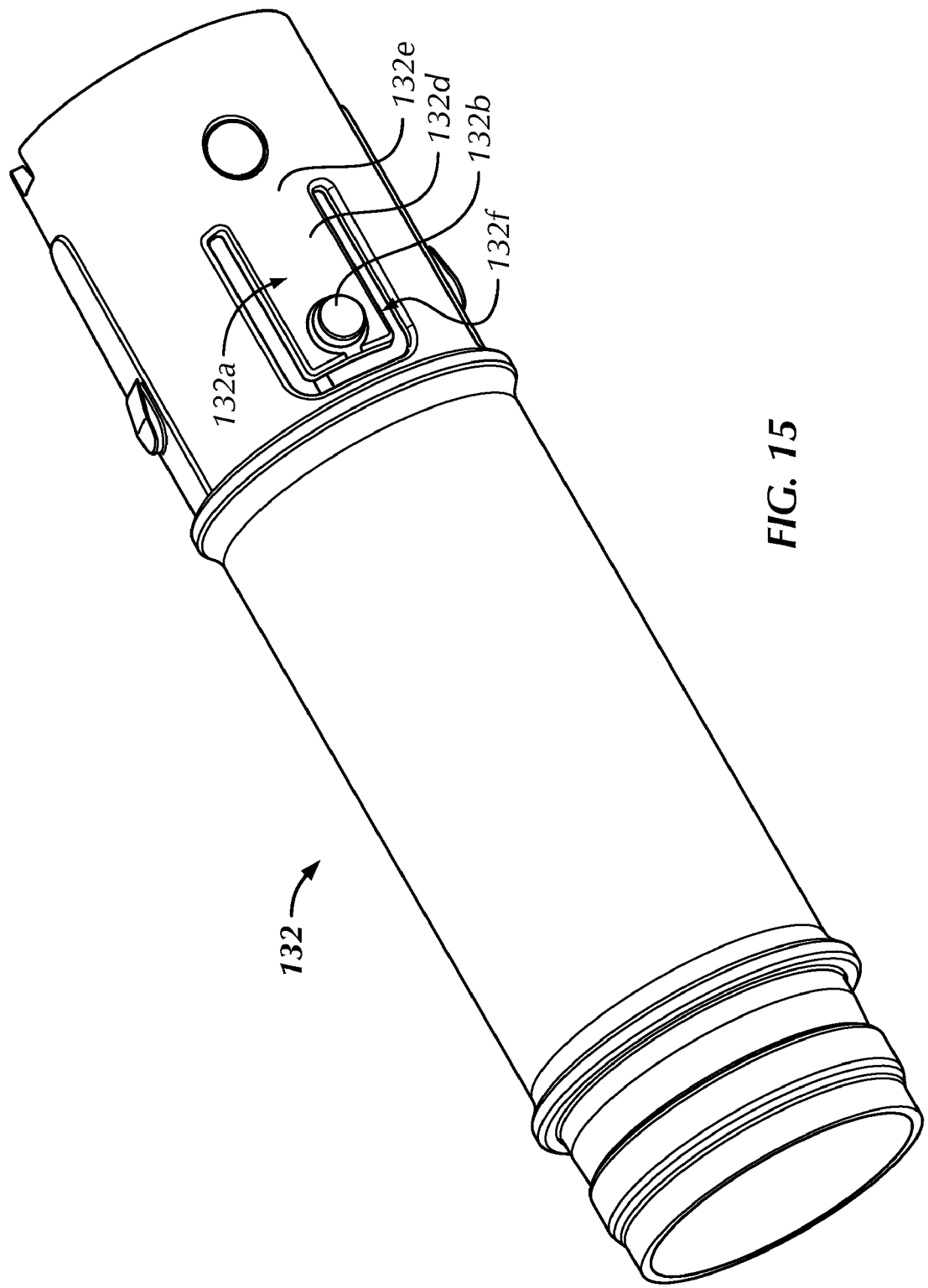
FIG. 15 is an enlarged perspective view of a tubular sleeve of the injector apparatus of FIG. 12.
Figure 16:
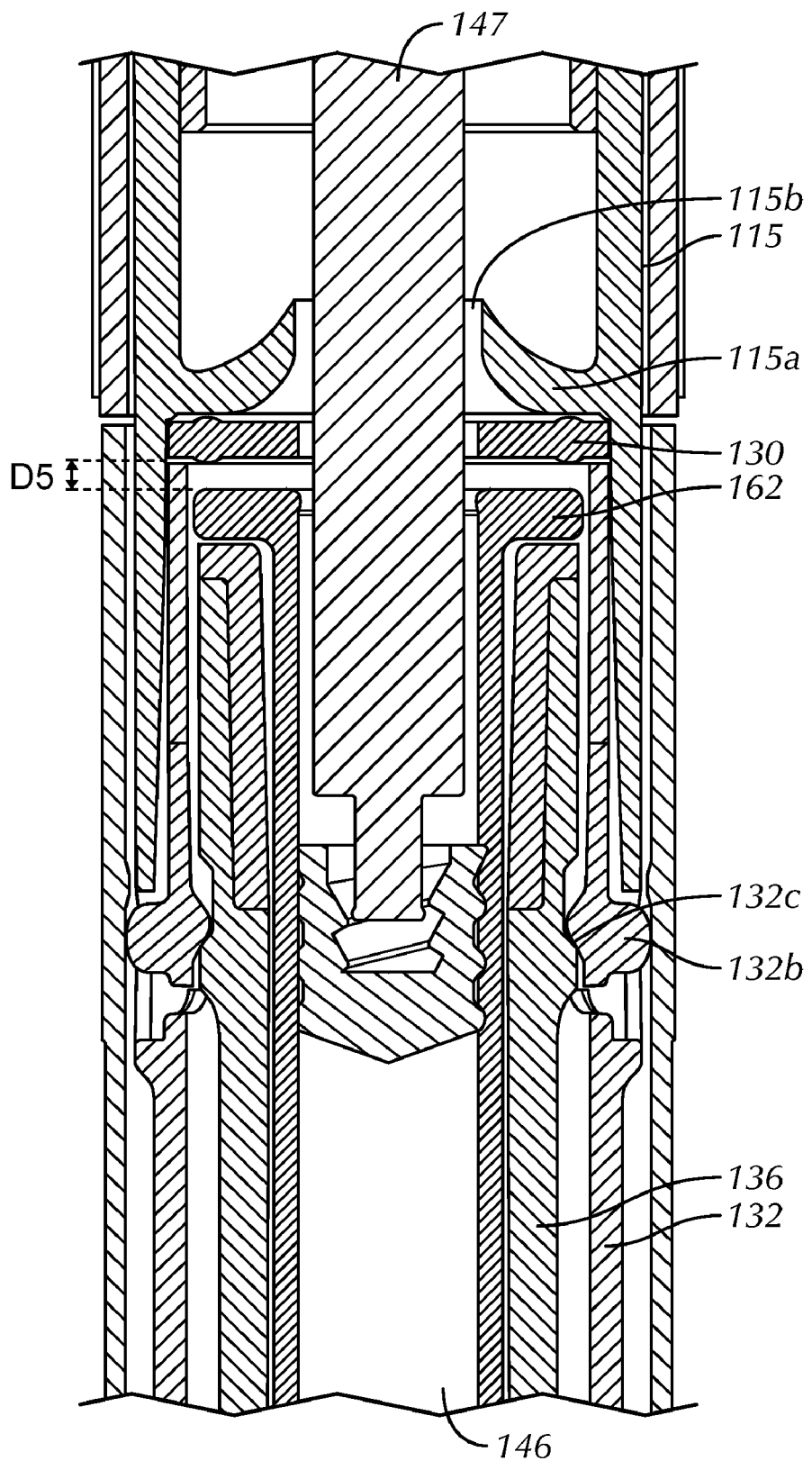
FIG. 16 is an enlarged, partial, cross-sectional, elevational view of a middle portion of the injector apparatus of FIG. 12.

The mid housing 128 includes a transverse surface 115a about its distal end that extends radially inwardly from a side wall surface of the mid housing 128, as best shown in FIG. 16. The transverse surface 115a includes an opening 115b concentric with the center of the transverse surface 115a. The opening 115b allows for the passage of a plunger rod 147 therethrough. In sum, the transverse surface 115a is a radially inwardly extending surface that extends from the sidewall of the proximal housing 115. The proximal housing 115 also includes a distal end depending distally relative to the transverse surface 115a. The distal end includes an aperture 113b (FIG. 13) that receives and allows for a radially outwardly extending protrusion 132b of a deflectable member 132a (FIG. 15) to protrude therefrom, as further described below.

Figure 14:
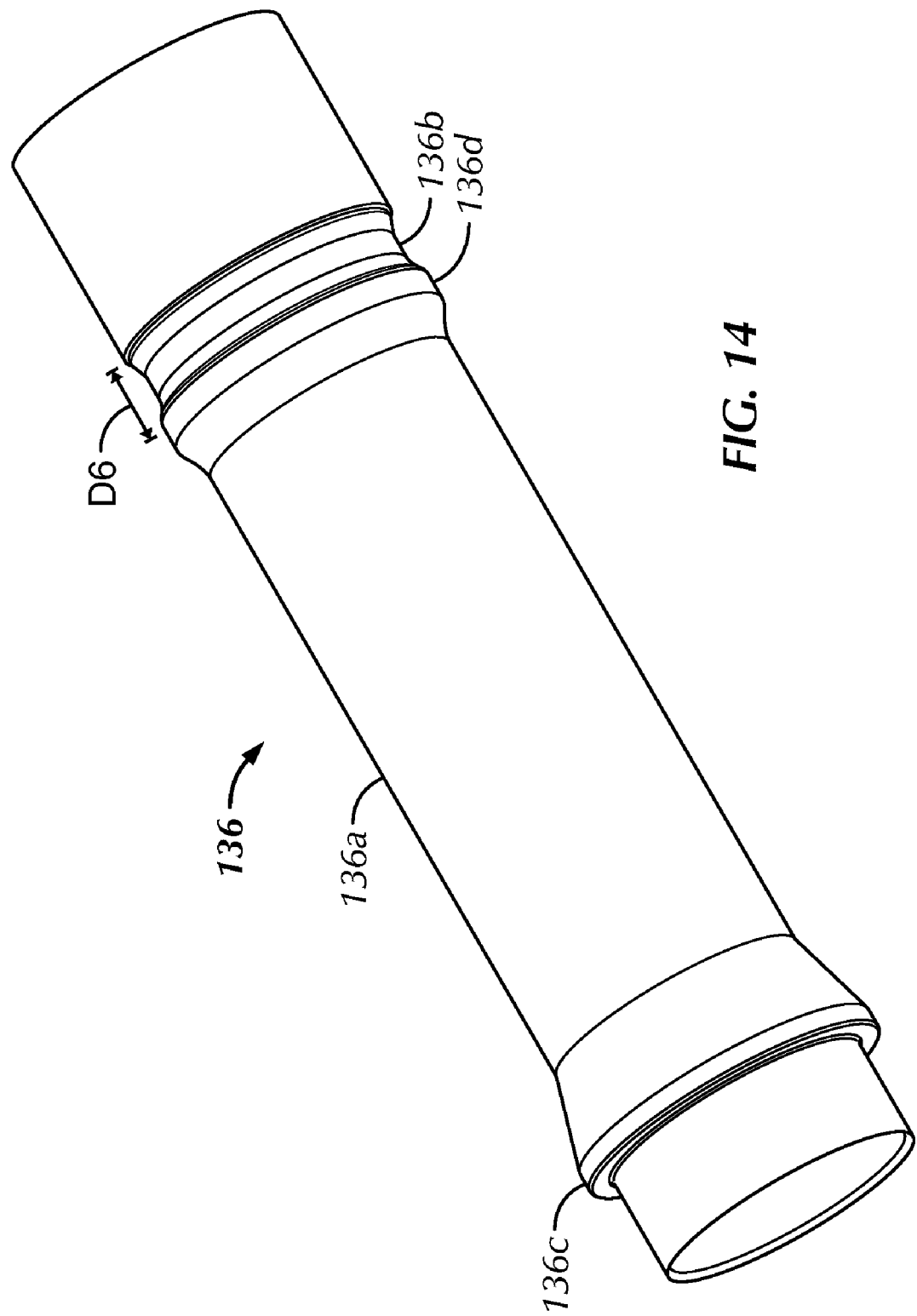
FIG. 14 is an enlarged perspective view of a syringe guide of the injector apparatus of FIG. 12.
Figure 17:
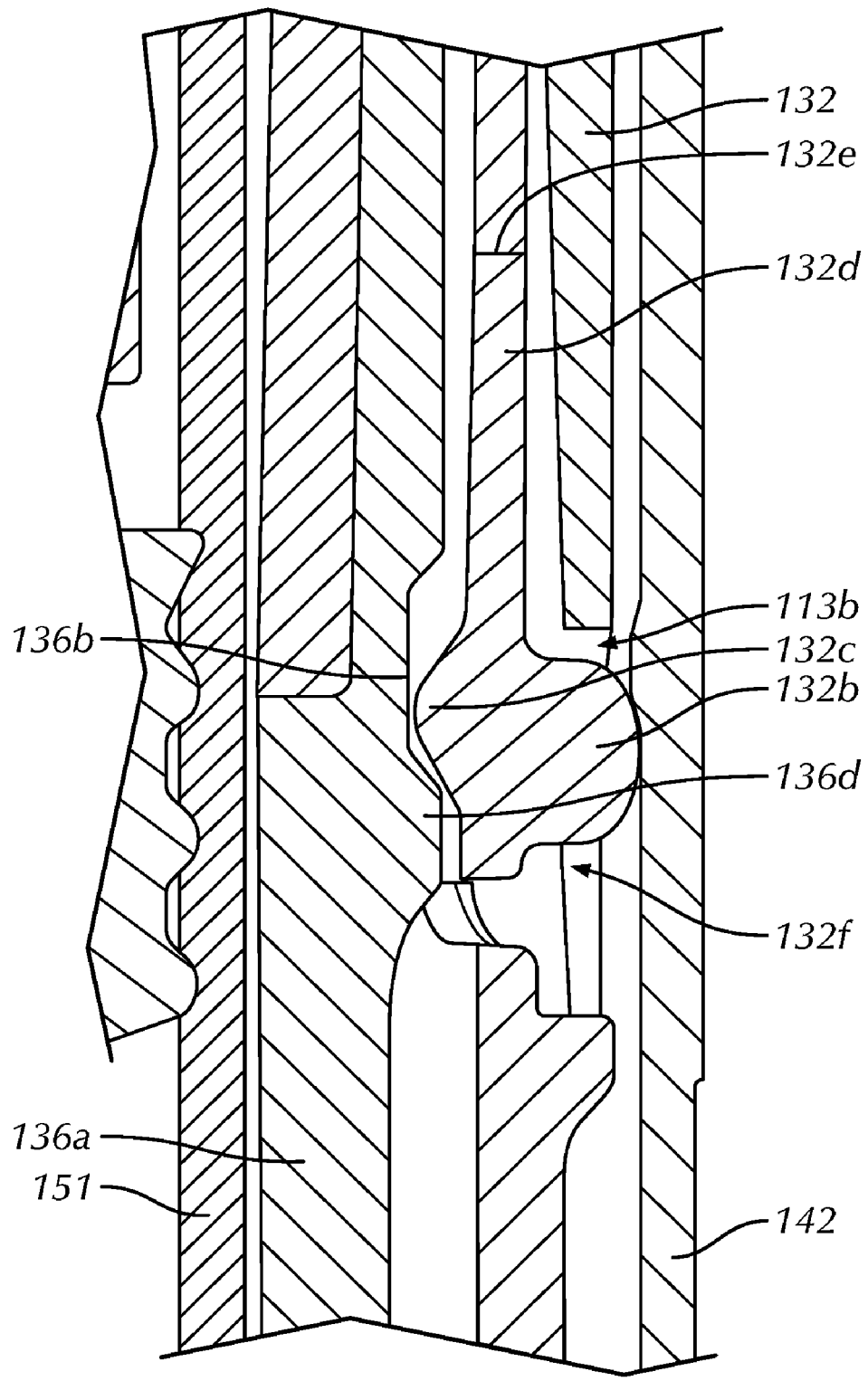
FIG. 17 is another enlarged, partial, cross-sectional, elevational view of a middle portion of the injector apparatus of FIG. 12.

The tubular syringe guide 136 (FIG. 14) is housed within the housing 113 to receive a syringe barrel 151. In particular, the syringe guide 136 is housed within the distal housing 117, as best shown in FIGS. 1 and 12. The tubular syringe guide 136 is generally configured as a tubular member having a tubular body 136a (FIG. 14). The tubular syringe guide 136 also includes a recess 136b about a proximal end of the tubular body 136a and a radially outwardly extending flange 136c about its distal end. Preferably, the recess 136b is configured as a circumferential groove. A circumferential rib 136d extends from the proximal end of the syringe guide 136. Specifically, as best shown in FIG. 17, the annular rib 136d forms a boundary for the recess 136b and is positioned distal to the recess 136b.

The distal housing 117 includes a tubular sleeve 132 (FIG. 15). The tubular sleeve 132 forms part of the distal housing 117 and is distal to the transverse surface 115a of the proximal housing 115. In particular, a proximal end of the tubular sleeve 132 partially overlaps with the distal end of the proximal housing 115 (FIG. 16). Such overlap occurs about an area distal to the transverse surface 115a. The tubular sleeve 132 is also configured to receive the syringe guide 136, such that the tubular syringe guide 136 is slidable relative to the tubular sleeve 132. As best shown in FIGS. 15-18, the tubular sleeve 132 includes a deflectable member 132a. Preferably, the tubular sleeve 132 includes a plurality of the deflectable members 132a that are circumferentially spaced apart about the tubular sleeve 132. The deflectable member 132a is preferably integrally formed as part of the wall of the tubular sleeve 132.

The deflectable member 132a is configured, as best shown in FIG. 15. In particular, the deflectable member 132a includes an elongated body 132d having a first end 132e connected to the tubular sleeve 132 and a second end 132f opposite to the first end. The second end 132f is a free end that is deflectable relative to the first end 132e. The second end 132f of the elongated deflectable member 132a also includes a radially inwardly extending protrusion 132c (FIG. 17) and a radially outwardly extending protrusion 132b. Preferably, the radially inward protrusion 132c is directly opposite the radially outward protrusion 132b. Each of the radially inwardly and outwardly protrusions 132c, 132b is configured, as best shown in FIG. 17. When deflected radially outwardly, the radially outward protrusion 132b protrudes out through aperture 113b and the radially inward protrusion 132c is out of the groove 136b (FIG. 19A).

Figure 18:
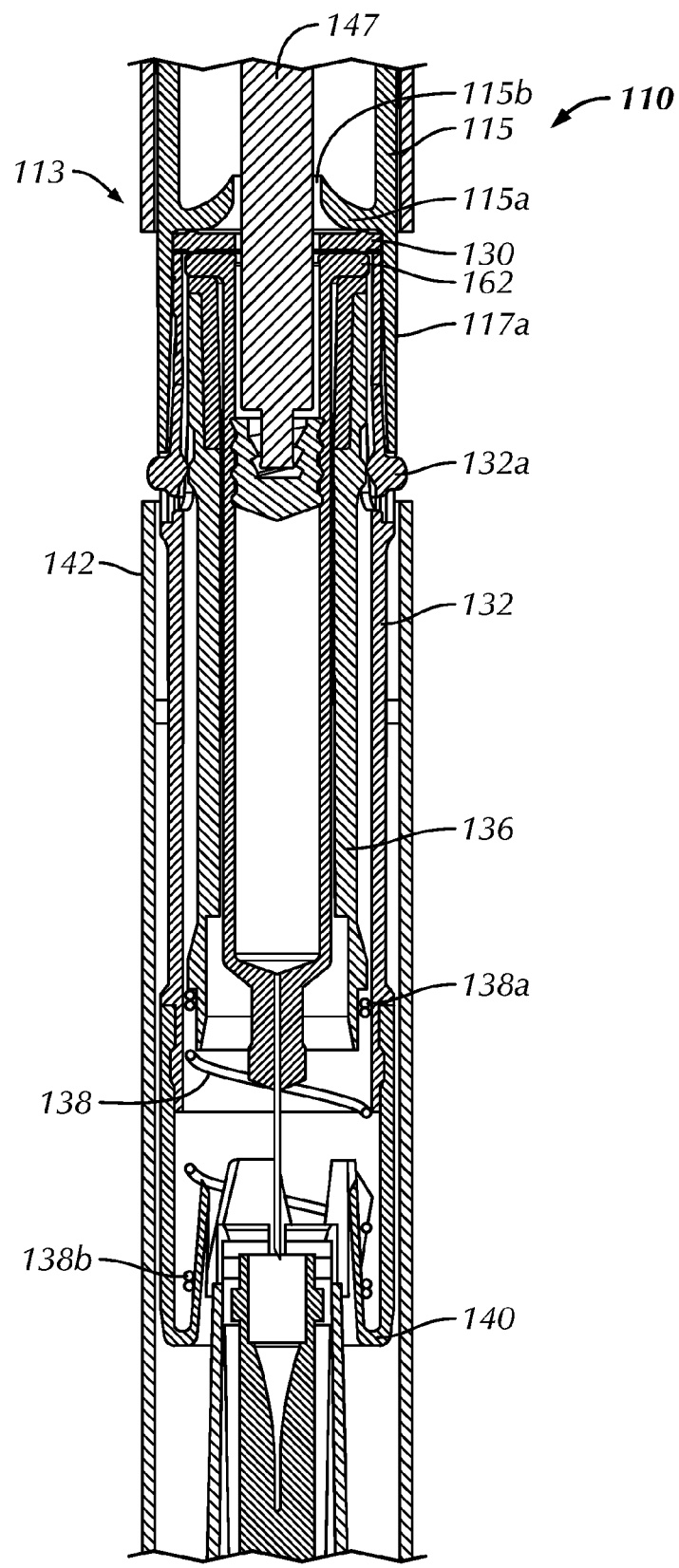
FIG. 18 is an enlarged, partial, cross-sectional, elevational view of a middle portion of the injector apparatus of FIG. 12 with the guard partially removed from the housing.

Referring to FIG. 18, the biasing member 138 is assembled to the injector apparatus 110 about the distal end of the housing 113. The biasing member 138 can be any biasing member generally known in the art, such as a compression spring, a constant force spring, or the like. Preferably, the biasing member 138 is a coil compression spring. The spring 138 includes a first end 138a that engages the radially outwardly extending flange 136c of the tubular syringe guide 136. The spring 138 also includes a second end 138b that engages the distal end of the housing 113. In general, the spring 138 is positioned between the radially outwardly extending flange 136c and an inner surface of the nose 140 (FIG. 12), such that the spring 138 is under compression.

Figure 8:
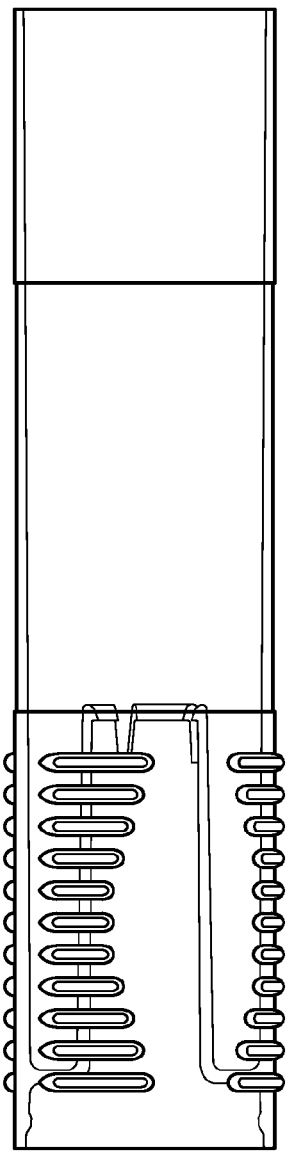
FIG. 8 is an enlarged side elevational view of the handle of FIG. 6.
Figure 9:
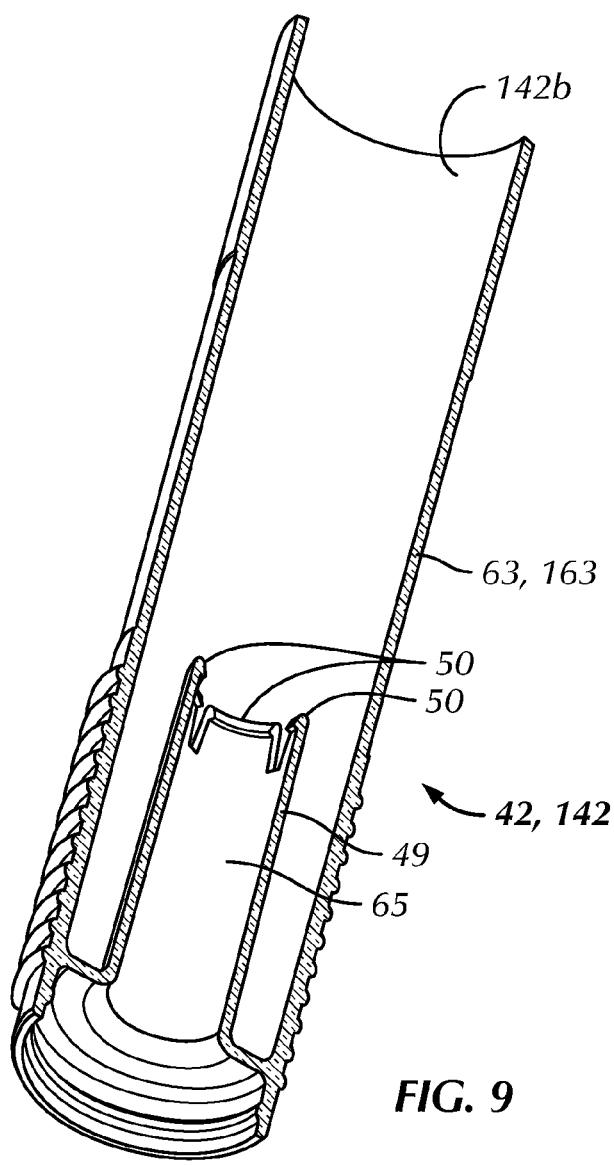
FIG. 9 is a cross-sectional perspective view of the handle of FIG. 8.
Figure 10:
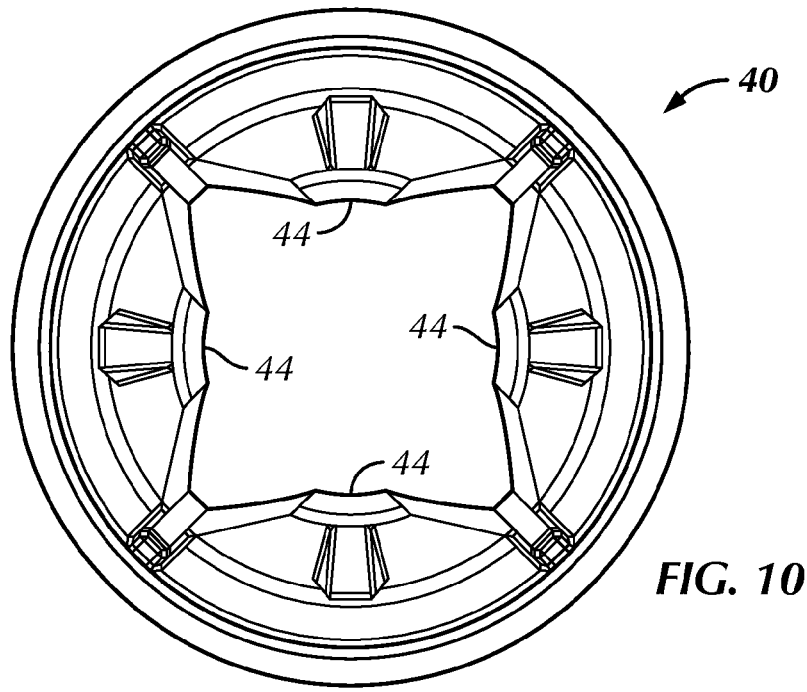
FIG. 10 is a top plan view of a nose of the autoinjector of FIG. 3.

The guard 142 is generally configured, as best shown in FIGS. 8 and 9, and includes a tubular guard body 163. The guard 142 is configured to receive the distal end of the injector apparatus 110 and in particular, to receive the tubular sleeve 132, tubular syringe guide 136, and syringe 146. FIG. 12 illustrates the injector apparatus 110 with the guard 142 fully assembled and seated on the distal end of the housing 113 in an initial position. The guard 142 is releasably connected to the distal end of the housing 113. In other words, the guard body 142a receives the deflectable member 132a and the syringe guide 136 to releasably hold the syringe guide 136 in an axial position against the biasing force of the spring 138.

Figure 19:
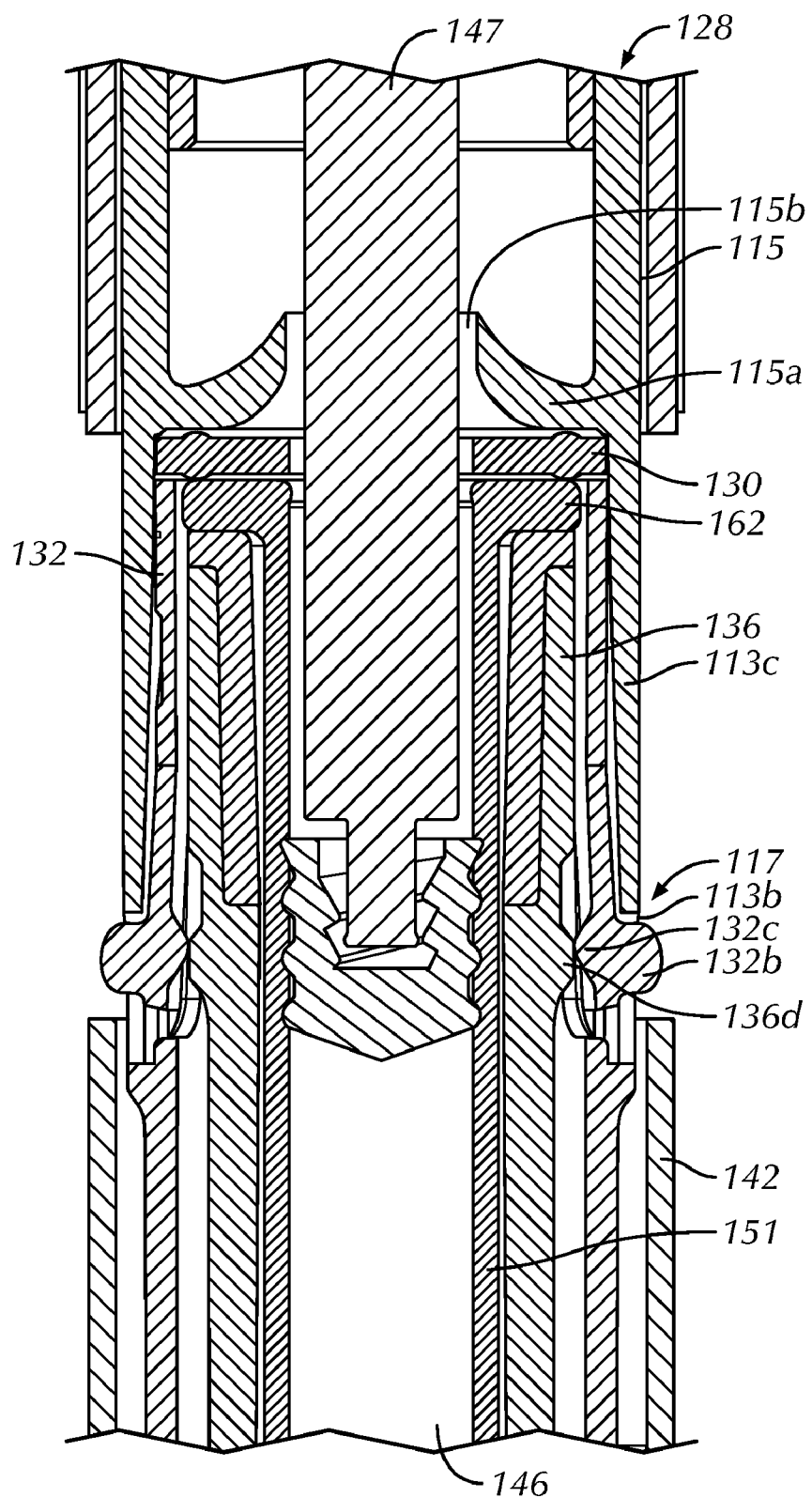
FIG. 19 is another enlarged, partial, cross-sectional, elevational view of a middle portion of the injector apparatus of FIG. 12 with the guard partially removed from the housing.
Figure 19A:
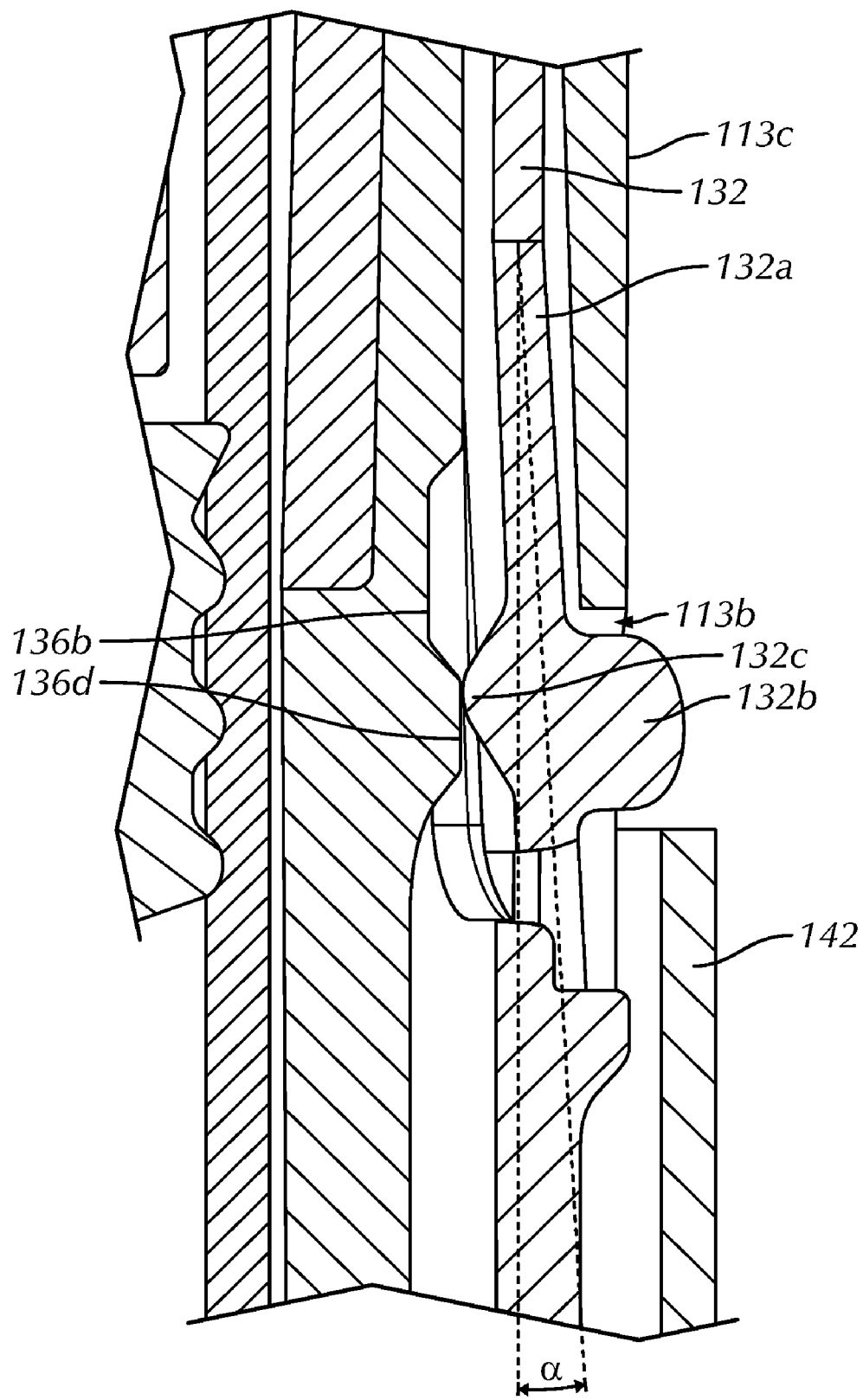
FIG. 19A is yet another enlarged, partial, cross-sectional, elevational view of a middle portion of the injector apparatus of FIG. 12 with the guard partially removed from the housing.

Referring to FIG. 12, the syringe barrel 151 is assembled within the tubular syringe guide 136 such that a syringe flange 162 is mounted or rested upon the proximal end of the syringe guide 136 (see also FIG. 19). The tubular syringe guide 136 is also assembled to reside within the tubular sleeve 132, such that the radially inward protrusion 132c resides within the recess 136b of the syringe guide 136 when in the initial position. The radially inward protrusion 132c is biased to reside within the recess 136b by an interior surface 142b (FIG. 9) of the guard 142 that biases or makes contact with the radially outward protrusion 132b of the deflectable member 132a. This assembly of the syringe guide 136, deflectable member 132a, and tubular sleeve 132 maintains the syringe guide 136, and hence the syringe 146, in a fixed axial position within the cylindrical housing 113. The assembly of the syringe guide 136, the tubular sleeve 132, and syringe 146 is configured such that a gap D5 is formed between a proximal surface of the syringe guide 136 and the transverse surface 115a, as shown in FIG. 16. The syringe guide 136 is biased in the proximal direction by the force of the spring 138, which thereby biases the entire assembly (i.e., syringe guide 136, tubular sleeve 132 and syringe 146) proximally. However, the assembly is fixed in position due to the radially inward protrusion 132c, which is held in place by the guard 142, residing within the recess 136b.

FIG. 18 shows the injector apparatus 110 with the guard 142 as it slides past the deflectable member 132a. In operation, as the guard 142 is withdrawn from the injector apparatus 110 and slides past to the deflectable member 132a, the deflectable member 132a is free to move and be biased in the radially outward direction by or as the syringe guide 136 is biased proximally due to the force of the biasing member 138a. That is, as the syringe guide 136 is biased in the proximal direction to close the gap D5 and engage the transverse surface 115a, the syringe guide 136 causes the deflectable member 132a and, in particular, the radially inward protrusion 132c to ride over and/or cam against the rib 136d of the syringe guide 136. After the syringe guide 136 is biased proximally such that the syringe guide 136 bottoms out against the transverse surface 115a, the radially inward protrusion 132c resides on the rib 136d (FIG. 19), such that the deflectable member 132a is biased radially outwardly through the aperture 113b. As the deflectable member 132a is biased outwardly by the rib 136d, the elongated body 132d forms an axial angle $\alpha$ (FIG. 19A) with respect to an exterior wall 113c of the cylindrical housing 113, such as a non-parallel angle with respect to the exterior wall 113c. The radially outward protrusion 132b extends out through the aperture 113b of the housing 113 so as to extend beyond the exterior wall 113c of the housing 113. The extension of the radially outward protrusion 132b beyond the exterior wall 113c impedes or resists the guard 142 from being fully reseated on the housing 113 after use.

In sum, the deflectable member 132a is movable between a biased inward position and a biased outward position. In the biased inwardly position, the radially inward protrusion 132c resides within the recess 136b of the syringe guide 136 and between the syringe guide 136 and the guard 142 to releasable hold the syringe guide 136 from moving in an axial direction. The deflectable member 132a is moved to the biased outward position when the guard 142 is removed from the housing 113 and the syringe guide 136 is biased proximally by the spring 138. In the biased outward position, the radially inward protrusion 132c engages an exterior surface of the tubular body 136a spaced apart from the recess 136b and the radially outward protrusion 132b extends beyond the exterior surface 113c of the housing 113. Preferably, in the biased outward position, the radially inward protrusion 132c contacts a radially protruding rib 136d on the exterior surface of the syringe guide 136 to prevent the elongated body 132d from deflecting inwardly. In addition, in the biased inward position, the syringe guide 136 and the syringe 146 are spaced apart from the transverse surface 115a of the proximal housing 117. Then, as the deflectable member 132a is moved to the biased outward position, the syringe 146 moves proximally to engage the transverse surface 115a of the proximal housing 117.

Alternatively, the injector apparatus 110 can include a syringe ring 130 about the proximal end of the distal housing 117 or the distal end of the proximal housing 115 (FIGS. 16 and 19). The syringe ring 130 circumscribes the plunger rod 147 and is positioned between a flange 162 of the syringe 146 and the transverse surface 115a. As such, when the deflectable member 132a is moved to the biased outward position, the syringe 146 moves proximally to engage the transverse surface 115a via the syringe ring 130.

Referring back to FIG. 16, the distal housing 117 includes the axially extending gap D5 having a fixed axial length such that a proximal surface of the syringe flange 162 can travel proximally upon the guard 142 being removed from the injector apparatus 110. When the injector apparatus 110 includes a syringe ring 130 that is adjacent to and in contact with the transverse surface 115a, the axially extending gap D5 extends from the bottom of the syringe ring 130 to the top of the syringe flange 162. The gap D5 has an axial length that is substantially equal to a width D6 (FIG. 14) that extends in the axial direction of the recess 136b of the syringe guide 136. Having the gap distance D5 and the width D6 of the recess 136b being substantially equal allows for the proper placement and positioning of the rib 136d to contact the radially inward protrusion 132c of the deflectable member 132a upon the syringe flange 162 bottoming out or engaging the transverse surface 115a.

Accordingly, the present invention advantageously provides for an injector apparatus 110 having a means to impede the axial movement of the syringe 146 until the needle shield is removed. That is, owing to the compressive force on the deflectable member 132a inwardly by engagement with the guard 142, the syringe guide 136, which receives the syringe 146, is releasably held in a fixed position along the axial direction within the injector apparatus 110. Then, when the guard 142 is removed, the syringe guide 136 slides upwardly due to the force of the spring 138, which thereby causes the radially inward protrusion 132c of the deflectable member 132a to ride up and out of the recess 136b and onto the rib 136d. As a result, the deflectable member 132a is angled radially outwardly with respect to a central axis of the housing 113 or the exterior wall of the housing 113 such that the radially outward protrusion 132b extends past the exterior wall surface 113c. Thus, the protruding radially outward protrusion 132b impedes and/or resists the guard 142 from being reseated on the injector apparatus 110. Consequently, the present invention provides a tamper evidence means to determine whether or not the injector apparatus 110 has been tampered with or previously used.

Additionally, should a user forcibly reseat the guard 142 onto the injector apparatus 110 past the radially outwardly extending protrusion 132b, the radially outward protrusion 132b serves to lock the guard 142 in place. That is, forcibly reseating the guard 142 onto the apparatus 110 creates a significant increase in the wedging force created by the interaction of the guard 142 and the radially outwardly protrusion 132b, so as to essentially form an encapsulated spent injector apparatus 110. Such an encapsulated injector apparatus 110 requires significant force to remove the guard 142, thereby further providing the user with an indication that the device has already be used or tampered with.

It will be appreciated by those skilled in the art that changes could be made to the embodiment described above without departing from the broad inventive concept thereof. It is understood, therefore, that this invention is not limited to the particular embodiment disclosed, but is intended to cover modifications within the spirit and scope of the present invention as defined by the claims.

What is claimed is:

1. An injector apparatus comprising:
    a cylindrical housing that includes a deflectable member, the deflectable member having:
        a radially outward protrusion, and
        a radially inward protrusion;
    a tubular syringe guide housed within the housing to receive a syringe barrel, the syringe guide including:
        a tubular body,
        a recess about a proximal end of the tubular body, and
        a radially outwardly extending flange about a distal end of the tubular body;
    a biasing member that includes:
        a first end that engages the radially outwardly extending flange, and
        a second end that engages a distal end of the housing; and
    a guard releasably connected to the distal end of the housing, the guard includes a tubular guard body to receive the deflectable member and the syringe guide, the deflectable member being movable between a biased inward position with the radially inward protrusion residing within the recess of the syringe guide and between the syringe guide and the guard to releasably hold the syringe guide from moving in an axial direction and a biased outward position when the guard is removed from the housing in which the radially inward protrusion engages an exterior surface of the tubular body spaced apart from the recess and the radially outward protrusion extends beyond an exterior surface of the cylindrical housing to impede the guard from being fully reseated on the housing.

2. The injector apparatus of claim 1, wherein the cylindrical housing comprises a plurality of circumferentially spaced deflectable members.

3. The injector apparatus of claim 1, wherein the deflectable members are integrally formed with the cylindrical housing.

4. The injector apparatus of claim 1, wherein the deflectable member is biased inwardly by the guard to releasably hold the injector apparatus in the biased inward position.

5. The injector apparatus of claim 1, wherein the deflectable member comprises an elongated body that includes:
    a first end connected to the housing; and
    a second end opposite the first end, the second end having the radially inwardly protrusion opposite the radially outwardly protrusion.

6. The injector apparatus of claim 5, wherein in the biased outward position, the elongated body is at an angle with respect to an exterior wall of the cylindrical housing and the radially inward protrusion contacts a radially protruding rib on an exterior surface of the syringe guide to impede the elongated body from deflecting inwardly.

7. The injector apparatus of claim 1, wherein the biasing member moves the syringe guide proximally within the housing when the guard is removed from the housing.

8. The injector apparatus of claim 1, wherein the biasing member is a spring.

9. An injector apparatus comprising:
    a cylindrical housing that includes:
        a proximal housing having:
            a transverse surface, and
            an opening through the transverse surface for the passage of a plunger rod, and
        a distal housing connected to the proximal housing, the distal housing including a plurality of deflectable members distal to the proximal housing, each deflectable member having:
            a radially outward protrusion, and
            a radially inward protrusion;
    a tubular syringe guide housed within the distal housing to receive a syringe body and slidable relative to the distal housing, the syringe guide including:
        a tubular body,
        a recess about a proximal end of the tubular body, and a distal end that engages a biasing member to slide the syringe guide in the proximal direction relative to the distal housing; and a guard releasably connected to the distal housing, the guard includes a tubular guard body to receive the plurality of deflectable members, each deflectable member being movable between a biased inward position with each radially inward protrusion residing within the recess of the syringe guide and between the syringe guide and the guard to releasably hold the syringe guide from moving in an axial direction and a biased outward position in which each radially inward protrusion engages an exterior surface of the tubular body spaced apart from the recess and the radially outward protrusion extends beyond an exterior surface of the distal housing when the guard is removed from the distal housing to impede the guard from being fully reseated on the housing.

10. The injector apparatus of claim 9, wherein the plurality of deflectable members are circumferentially spaced apart.

11. The injector apparatus of claim 9, wherein the plurality of deflectable members are integrally formed with the distal housing.

12. The injector apparatus of claim 9, wherein the plurality of deflectable members are biased to the biased inwardly position by the guard to releasably hold the injector apparatus.

13. The injector apparatus of claim 9, wherein the plurality of deflectable members each comprise an elongated body that includes:

a first end connected to the distal housing; and a second end opposite the first end, the second end having a radially inwardly extending protrusion opposite the radially outwardly extending protrusion.

14. The injector apparatus of claim 13, wherein in the biased outward position, the elongated body is at an axial angle with respect to an exterior surface of the distal housing and the radially inward protrusion contacts a radially protruding rib on an exterior surface of the syringe guide to prevent the elongated body from deflecting inwardly.

15. The injector apparatus of claim 9, wherein in the biased inward position, the syringe guide and syringe body are spaced apart from the transverse surface of the proximal housing and in the biased outward position, the syringe guide and syringe body engage the transverse surface of the proximal housing.

16. The injector apparatus of claim 9, wherein the biasing member moves the syringe guide proximally within the distal housing when the guard is removed from the housing.

17. The injector apparatus of claim 9, wherein the biasing member is a spring.

18. An injector apparatus comprising:
a cylindrical housing that includes:
a transverse surface internal to the cylindrical housing, the transverse surface having an opening for the passage of a plunger rod, and
an aperture along a side wall of the housing distal to the transverse surface;
a tubular sleeve connected to and at least partially housed within the cylindrical housing distal to the transverse surface, the tubular sleeve includes a deflectable member;
a tubular syringe guide housed within the tubular sleeve to receive a syringe body and being slidable relative to the tubular sleeve, the syringe guide includes:
a proximal end having a recess, and
a distal end that engages a biasing member to slide the syringe guide in the proximal direction relative to the tubular sleeve;
a guard releasably connected to the cylindrical housing, the guard includes a tubular guard body to receive a distal end of the cylindrical housing and the deflectable member,
wherein the deflectable member includes:
a radially inward protrusion that resides within the recess of the syringe guide, and
a radially outward protrusion that extends through the aperture of the cylindrical housing and directly engages an interior surface of the guard to releasably hold the syringe guide from moving in an axial direction.

19. The injector apparatus of claim 18, wherein the deflectable member is movable between a biased inwardly position with the radially inward protrusion residing within the recess and the syringe guide and syringe body are spaced apart from the transverse surface and a biased outward position when the guard is removed from the housing in which the radially inward protrusion engages a rib on an exterior surface of the syringe guide spaced apart from the recess and the syringe guide and syringe body engage the transverse surface.

20. The injector apparatus of claim 18, wherein the deflectable member is integrally formed with the tubular sleeve.

21. The injector apparatus of claim 18, wherein the syringe guide and syringe body are spaced apart from the transverse surface a fixed distance, and wherein the recess of the syringe guide has a width that extends in an axial direction substantially equal to the fixed distance.

22. The injector apparatus of claim 18, further comprising:
a syringe ring circumscribing the plunger rod and positioned between a flange of the syringe body and the transverse surface; and
a gap having a fixed axial length between a proximal surface of the syringe guide and the transverse surface,
wherein the recess of the syringe guide has a width that extends in an axial direction substantially equal to the gap.

23. The injector apparatus of claim 18, wherein the biasing member moves the syringe guide proximally within the tubular sleeve when the guard is removed from the housing.

* * * * *